(12) United States Patent
Sakai

(10) Patent No.: US 8,213,567 B2
(45) Date of Patent: Jul. 3, 2012

(54) RADIOGRAPHIC APPARATUS

(75) Inventor: Takihito Sakai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 184 days.

(21) Appl. No.: 12/672,272

(22) PCT Filed: Aug. 13, 2007

(86) PCT No.: PCT/JP2007/065828
§ 371 (c)(1),
(2), (4) Date: Feb. 4, 2010

(87) PCT Pub. No.: WO2009/022408
PCT Pub. Date: Feb. 19, 2009

(65) Prior Publication Data
US 2011/0228900 A1    Sep. 22, 2011

(51) Int. Cl.
*A61B 6/00* (2006.01)

(52) U.S. Cl. ............................. 378/10; 378/4; 382/132

(58) Field of Classification Search ................. 378/4, 8, 378/10; 382/132
See application file for complete search history.

(56) References Cited

U.S. PATENT DOCUMENTS

| | | | | |
|---|---|---|---|---|
| 6,097,833 | A * | 8/2000 | Lobregt et al. ............. | 382/130 |
| 6,459,094 | B1 * | 10/2002 | Wang et al. ................ | 250/584 |
| 6,587,598 | B1 | 7/2003 | Devillers et al. | |
| 2004/0101103 | A1 * | 5/2004 | Warp et al. ................ | 378/98.12 |
| 2004/0114717 | A1 * | 6/2004 | Kato .......................... | 378/62 |
| 2004/0228438 | A1 * | 11/2004 | Sukeyasu et al. .......... | 378/62 |
| 2004/0247081 | A1 | 12/2004 | Halsmer et al. | |
| 2005/0129298 | A1 * | 6/2005 | Warp et al. ................ | 382/132 |
| 2005/0129299 | A1 * | 6/2005 | Kreang-Arekul et al. .... | 382/132 |
| 2005/0169427 | A1 | 8/2005 | Halsmer et al. | |
| 2006/0018527 | A1 * | 1/2006 | Bojer et al. ............... | 382/132 |
| 2010/0189214 | A1 * | 7/2010 | Shibata et al. ............. | 378/21 |

FOREIGN PATENT DOCUMENTS

| | | |
|---|---|---|
| JP | 2000-350717 A | 12/2000 |
| JP | 2001-269333 A | 10/2001 |
| JP | 2002-537050 A | 11/2002 |
| JP | 2003-52680 A | 2/2003 |
| JP | 2004-113408 A | 4/2004 |
| JP | 2004-236929 A | 8/2004 |
| JP | 2004-358255 A | 12/2004 |
| JP | 2005-46444 A | 2/2005 |
| JP | 2005-270277 A | 10/2005 |
| JP | 2005-296332 A | 10/2005 |
| JP | 2006-71472 A | 3/2006 |

OTHER PUBLICATIONS

International Search Report for the Application No. PCT/JP2007/065828 mailed Nov. 13, 2007.

* cited by examiner

*Primary Examiner* — Alexander H Taningco
(74) *Attorney, Agent, or Firm* — Cheng Law Group, PLLC

(57) ABSTRACT

In the radiographic apparatus of this invention, when obtaining long images in a longitudinal direction, a correcting device corrects radiographic images based on overlapping areas of a plurality of radiographic images based on the radiation detected whenever a relative movement is made in the same direction, an image decomposing device decomposes corrected radiographic images for every predetermined distance, and an image composing device composes the decomposed images for each of the same projection angles to obtain a projection image for each projection angle. Thus, with a reconstruction processing device carrying out a reconstruction process based on the composed projection images, sectional images having a long field of view in the longitudinal direction can be obtained, while reducing luminance differences among different radiographic images.

9 Claims, 9 Drawing Sheets

RADIOGRAPHIC APPARATUS

TECHNICAL FIELD

This invention relates to a radiographic apparatus for carrying out a radiation image pickup by obtaining radiographic images based on radiation detected, and more particularly to a technique for obtaining sectional images through a reconstruction process.

BACKGROUND ART

Radiographic apparatus which obtain sectional images through a reconstruction process include an X-ray CT (computed tomography) apparatus and an X-ray tomography (includes tomosynthsis) apparatus. In the X-ray CT apparatus, sectional images are obtained by an X-ray tube (radiation emitting device) and an X-ray detector (radiation detecting device) rotating about the body axis extending longitudinally of a patient. In the X-ray tomography apparatus, as shown in FIG. 11, for example, sectional images are obtained by an X-ray tube 101 and an X-ray detector 102 making parallel translation in opposite directions along the body axis z of a patient M. In the case of the X-ray tomography apparatus, compared with the X-ray CT apparatus, the resolution in the depth direction of sectional images obtained is inferior, but there are advantages that the resolution in the in-plane direction is superior, and that sectional images can be obtained also in a standing position. The image pickup mode adopted in such X-ray CT apparatus and X-ray tomography apparatus is an image pickup method effective for many sites such as the chest, joints and digestive organs.

On the other hand, there has been an X-ray apparatus in recent years which obtains X-ray images along the body axis of a patient by moving an X-ray tube and an X-ray detector in parallel to each other in the same direction along the body axis of the patient (see Patent Document 1, for example). The X-ray images obtained with this apparatus are projection data of projected X-rays (projection images). Since the X-ray tube and X-ray detector move parallel to each other in the same direction along the body axis, the projection angle can be maintained at substantially the same angle. Therefore, X-ray images can be obtained of a long area (long X-ray images) in the longitudinal direction which is the direction of the body axis.

[Patent Document 1]
Unexamined Patent Publication No. 2004-236929 (pages 1-8, FIGS. 1, 6 and 10)

DISCLOSURE OF THE INVENTION

Problem to be Solved by the Invention

However, the above X-ray tomography apparatus has a limited field of view. An image intensifier (I. I) or the like was used as the X-ray detector in the past, but in recent years a flat panel X-ray detector (hereinafter abbreviated as "FPD") has been used as shown in FIG. 11. The FPD, with the detecting plane being a flat plane, has a larger field of view than the image intensifier. However, with the X-ray tomography apparatus, the farther from the central cutting plane, the narrower becomes the effective field of view size. As a result, the field of view is limited even when the FPD is used as the X-ray detector. Thus, tomography with a field of view long in the direction of the body axis is desired.

Then, Applicant has directed its attention to an X-ray apparatus which obtains X-ray images long in the longitudinal direction as in Patent Document 1 noted above, and has proposed the following technique (Patent Application No. 2006-215982). That is, whenever a radiation emitting device (X-ray tube 2 in FIG. 6) and a radiation detecting device (flat panel X-ray detector 3: FPD 3 in FIG. 6) move every predetermined distance (pitch d in FIG. 6) relative to a patient, radiation (X-rays) is emitted from the radiation emitting device (X-ray tube 2), and the radiation detecting device (FPD 3) detects radiation (X-rays) transmitted through the patient irradiated.

The apparatus includes an image decomposing device (image decomposing unit 9b in FIG. 1) for decomposing radiographic images ($O_1, O_2, \ldots, O_I, \ldots$ and $O_M$, where $1 \leq I \leq M$, in FIG. 6) for every predetermined distance (pitch d), an image composing device (image composing unit 9c in FIG. 1) for composing the decomposed images (images $O_{11}, O_{12}, \ldots, O_{1J}, \ldots, O_{1(N-1)}$ and $O_{1N}$; images $O_{21}, O_{22}, \ldots, O_{2J}, \ldots, O_{2(N-1)}$ and $O_{2N}$; $\ldots$ ; images $O_{I1}, O_{I2}, \ldots, O_{IJ}, \ldots, O_{I(N-1)}$ and $O_{IN}$; $\ldots$ ; and images $O_{M1}, O_{M2}, \ldots, O_{MJ}, \ldots, O_{M(N-1)}$ and $O_{MN}$, in FIG. 6) for each of the same projection angles (projection angles $\theta_1, \Theta_2, \ldots, \theta_J, \ldots, \theta_{N-1}$ and $\theta_N$ in FIG. 6) to obtain a projection image (projection image $P_1, P_2, \ldots, P_J, \ldots,$ or $P_N$ in FIGS. 9 and 10) for each projection angle, and a reconstruction processing device (reconstruction processing unit 9d in FIG. 1) for carrying out a reconstruction process based on the composed projection images (projection images $P_1, P_2, \ldots,$ and $P_N$) to obtain a sectional image.

According to such technique, data with a field of view long in the longitudinal direction (body axis z in FIG. 1) can be obtained from the radiation detecting device (FPD 3), by constructing the radiation emitting device (X-ray tube 2) and the radiation detecting device (FPD 3) to be movable parallel relative to each other in the same direction along the longitudinal direction (body axis z) of the patient. On the other hand, whenever the radiation emitting device (X-ray tube 2) and the radiation detecting device (FPD 3) move every predetermined distance (pitch d), the radiation emitting device (X-ray tube 2) emits radiation (X-rays) and the radiation detecting device (FPD 3) detects radiation (X-rays) transmitted through the patient irradiated. And the image decomposing device (image decomposing unit 9b) decomposes the radiographic images (X-ray images) for the every predetermined distance (pitch d), and the image composing device (image composing unit 9c) composes the decomposed images for each of the same projection angles to obtain a projection image for each projection angle. Thus, the reconstruction processing device (reconstruction processing unit 9d) carries out a reconstruction process based on the composed projection images, thereby to obtain a sectional image with a field of view long in the longitudinal direction.

However, with X-ray images $O_1, O_2, \ldots, O_I, \ldots,$ and $O_M$ obtained for every frame, differences (i.e. luminance differences) in pixel value among the frames due to variations in the output of an X-ray high-voltage generator appear as strip-shaped bright or dark regions on long sectional images, which have adverse influences also on an image after reconstruction.

This invention has been made having regard to the state of the art noted above, and its object is to provide a radiographic apparatus which can reduce luminance differences among different radiographic images.

Means for Solving the Problem

To fulfill the above object, this invention provide the following construction.

This invention provides a radiographic apparatus having a radiation emitting device for emitting radiation toward a patient, and a radiation detecting device for detecting radiation transmitted through the patient, to carry out radiographic image pickup by obtaining radiographic images based on the detected radiation, the radiation emitting device and the radiation detecting device being constructed movable parallel relative to each other in the same direction along a longitudinal direction of the patient, the radiation emitting device emitting radiation and the radiation detecting device detecting radiation transmitted through the patient irradiated while the radiation emitting device and the radiation detecting device move every predetermined distance relative to the patient, the apparatus comprising a correcting device for correcting radiographic images based on overlapping areas of a plurality of radiographic images based on the radiation detected whenever a relative movement is made in the same direction, an image decomposing device for decomposing corrected radiographic images for the every predetermined distance, an image composing device for composing the decomposed images for each of the same projection angles to obtain a projection image for each projection angle, and a reconstruction processing device for carrying out a reconstruction process based on the composed projection images to obtain a sectional image.

According to the radiographic apparatus of this invention, the radiation emitting device and the radiation detecting device are constructed movable parallel relative to each other in the same direction along the longitudinal direction of the patient, whereby data with a long field of view in the longitudinal direction can be obtained from the radiation detecting device. On the other hand, while the radiation emitting device and the radiation detecting device move every predetermined distance relative to the patient, radiation is emitted from the radiation emitting device and the radiation detecting device detects radiation transmitted through the patient irradiated. And the image decomposing device decomposes, for every predetermined distance noted above, the radiographic images based on the radiation detected whenever the relative movement is made in the same direction noted above. The image composing device composes the decomposed images for each of the same projection angles to obtain a projection image for each of the projection angles. Thus, with the reconstruction processing device carrying out a reconstruction process based on the composed projection images, sectional images having a long field of view in the longitudinal direction can be obtained.

The image decomposing device, image composing device and reconstruction processing device are the technique described in the paragraphs "Problem to Be Solved by the Invention". The radiographic apparatus of this invention provides the following construction before the image decomposing device decomposes radiographic images for every predetermined distance. That is, the correcting device corrects radiographic images based on overlapping areas of a plurality of radiographic images based on radiation detected whenever a relative movement is made in the same direction. The areas used in this correction are areas having strong correlativity, and since the correction is made taking such areas into consideration, luminance differences among different radiographic images can be reduced. And the image decomposing device decomposes such corrected radiographic images for every predetermined distance. The image composing device composes decomposed images for each of the same projection angles to obtain a projection image for each projection angle. The reconstruction processing device carries out a reconstruction process based on the composed projection images, thereby obtaining sectional images with a long field of view in the longitudinal direction while reducing the luminance differences among the different radiographic images.

In one example of this invention noted above, when K is a natural number, the correcting device is arranged, based on one radiographic image of radiographic images in two, frame K and frame (K+1) adjoining each other in time, to correct the other radiographic image. Through the correction using the radiographic images in such two, frame K and frame (K+1) adjoining each other in time, a luminance difference between the frames can be reduced.

Where the correction is made using the radiographic images in the two, frame K and frame (K+1) adjoining each other in time, the correcting device may be arranged to repeat a procedure in which, based on one radiographic image of radiographic images in two frame adjoining each other in time, including the corrected radiographic image, the other radiographic image is corrected. By making corrections in this way, the luminance differences among the frames can be reduced in the radiographic image in each frame.

The dose of the radiation is not stabilized for the first frame 1. Conversely, where the last frame is frame M, imperfect irradiation (exposure) can take place for frame M when, for example, the irradiation button is released during irradiation. It is therefore desirable not to make a correction using the first frame 1 or last frame M as reference. Thus, when the above M is a natural number satisfying K<M, the correcting device, (1) excluding the radiographic images in the first frame 1 and the last frame M, based on one radiographic image in frame K which is the frame preceding in time of the radiographic images in two, frame K and frame (K+1) adjoining each other in time, corrects the other radiographic image in frame (K+1) which is the frame succeeding in time. Then, (2) based on the above corrected one of the radiographic images which is the frame preceding in time of the radiographic images in two frames adjoining each other in time and including the corrected radiographic image in the frame preceding in time, the other radiation frame which is the frame succeeding in time is corrected. This procedure is repeated until the radiographic image in the last frame M is corrected.

Apart from the above, (3) excluding the radiographic images in the first frame 1 and the last frame M, based on one radiographic image in frame K which is the frame succeeding in time of the radiographic images in two, frame (K−1) and frame K adjoining each other in time, the other radiographic image in frame (K−1) which is the frame preceding in time is corrected. Then, (4) based on the above corrected one of the radiographic images which is the frame succeeding in time of the radiographic images in two frames adjoining each other in time and including the corrected radio-graphic image in the frames succeeding in time, the other radiation frame which is the frame preceding in time is corrected. This procedure is repeated until the radio-graphic image in the first frame 1 is corrected. Thus, through the corrections as in (1)-(4), the correcting device corrects the radiographic image in each frame using the radiographic image in frame K as reference. Since this frame K is neither the first frame 1 nor the last frame M, its radiographic image is appropriate as the reference, and therefore the corrections can be carried out appropriately.

It is preferable to carry out (1) and (3) above in parallel. The calculation time in the correcting device can be shortened by carrying out (1) and (3) in parallel. Of course, (3) and (4) may be carried out after (1) and (2). Conversely, (1) and (2) may be carried out after (3) and (4).

In the case where (1) and (3) are carried out in parallel, and when M is an odd number, it is preferable to determine a radiographic image acting as reference for the correction in a way to satisfy K=(M+1)/2. That is, since the radiographic image in frame K which satisfies K=(M+1)/2 is at the center in time, by carrying out (1) and (3) in parallel, the correction of the radiographic image in the last frame M in (2) and the correction of the radiographic image in the first frame 1 in (4) can be finished at the same time, and the calculation time in the correcting device can be shortened further.

In the case where (1) and (3) are carried out in parallel, and when M is an even number, it is preferable to determine an radiographic image acting as reference for the correction in a way to satisfy K=M/2+1 or K=M/2. That is, since the radiographic image in frame K which satisfies K=M/2+1 or K=M/2 is substantially at the center in time, by carrying out (1) and (3) in parallel, the correction of the radiographic image in the last frame M in (2) and the correction of the radiographic image in the first frame 1 in (4) can be finished substantially at the same time, and the calculation time in the correcting device can be shortened further.

In these inventions noted above, it is preferred that, from the overlapping areas of the plurality of radiographic images predetermined pixel areas smaller than the areas are selected, and the correcting device is arranged to correct the radiographic images based only on the selected pixel areas. By carrying out the correction without using all the overlapping areas, the arithmetic process by the correcting device can be made high-speed.

In these inventions noted above, it is preferred that the radiation emitting device and the radiation detecting device are movable parallel to each other at the same speed relative to the patient. With the radiation emitting device and the radiation detecting device moving parallel to each other at the same speed relative to the patient, the projection angle can be maintained at the same angle. The radiation emitting device and the radiation detecting device can be moved for a long time. As a result, sectional images with a longer field of view can be obtained.

Effects of the Invention

With the radiographic apparatus according to this invention, the radiation emitting device and the radiation detecting device are constructed movable parallel relative to each other in the same direction along the longitudinal direction of the patient. While the radiation emitting device and the radiation detecting device move every predetermined distance relative to the patient, radiation is emitted from the radiation emitting device and the radiation detecting device detects radiation transmitted through the patient irradiated. The correcting device corrects radiographic images based on overlapping areas of a plurality of radiographic images based on the radiation detected whenever a relative movement is made in the same direction. The image decomposing device decomposes the corrected radiographic images for every predetermined distance noted above. The image composing device composes the decomposed images for each of the same projection angles to obtain a projection image for each of the projection angles. Thus, with the reconstruction processing device carrying out a reconstruction process based on the composed projection images, sectional images having a long field of view in the longitudinal direction can be obtained, while reducing luminance differences among different radiographic images.

DESCRIPTION OF REFERENCES

Figure 1:
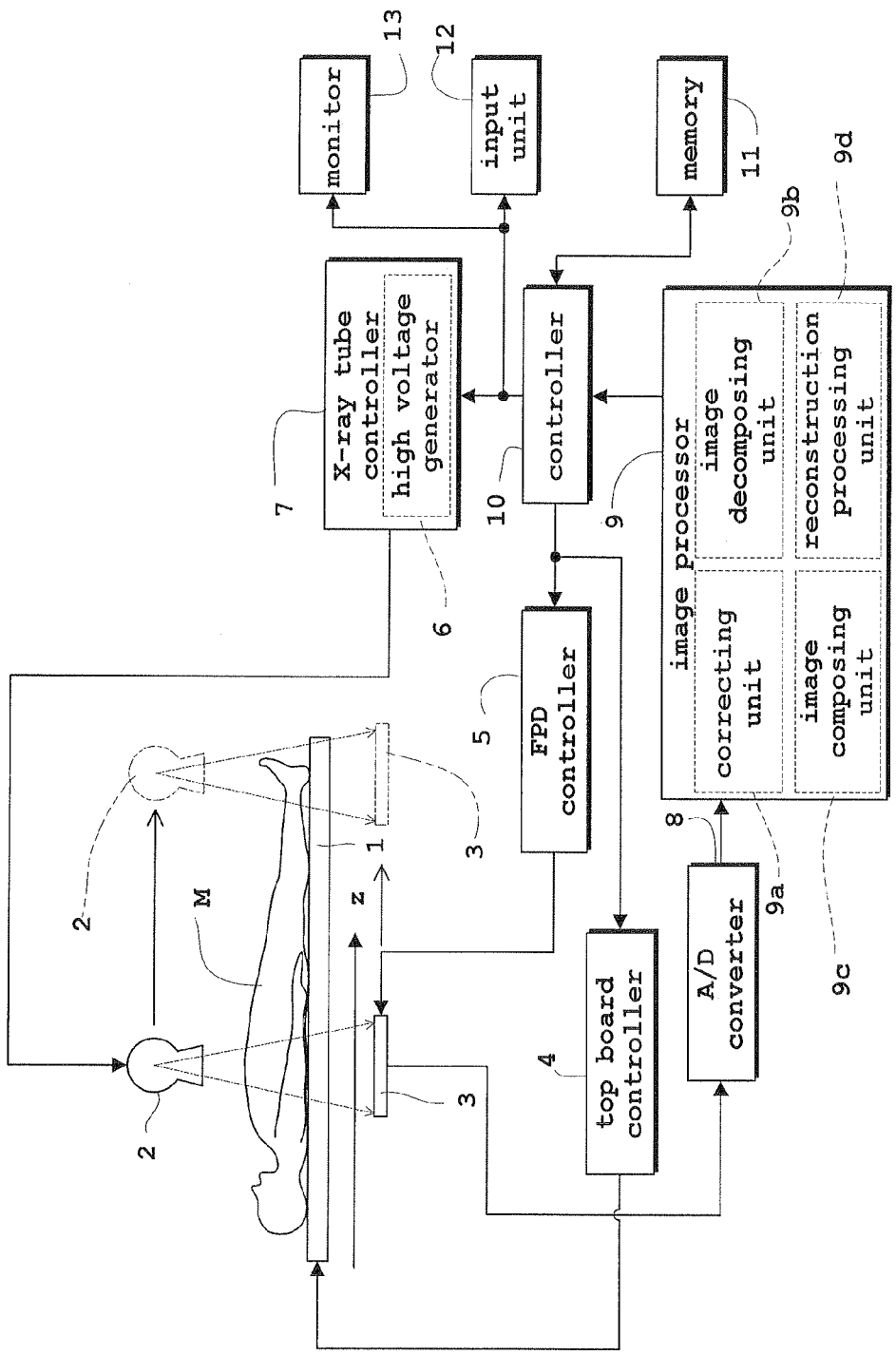
FIG. 1 is a block diagram of an X-ray tomography apparatus according to an embodiment.
Figure 2:
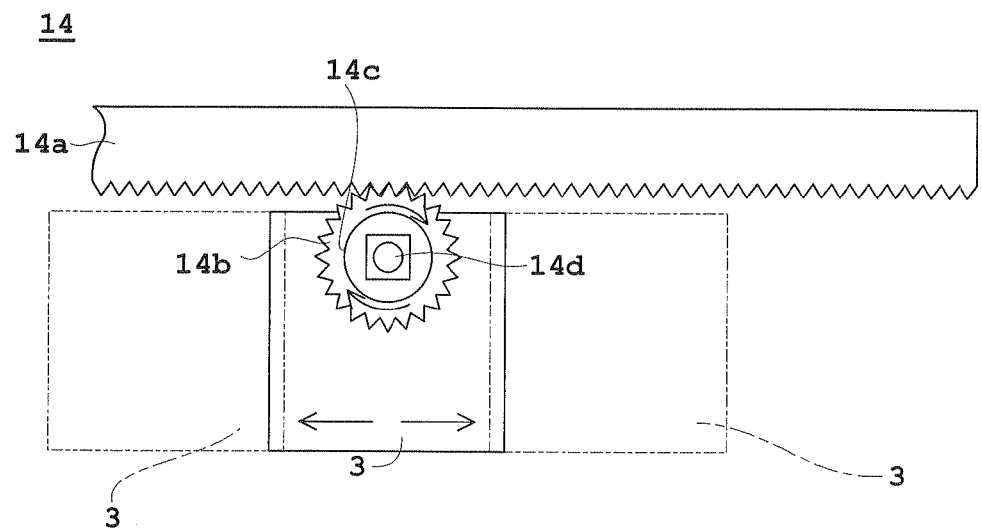
FIG. 2 is a schematic view showing an outline of an FPD drive mechanism relating to driving of a flat panel X-ray detector (FPD)
Figure 3:
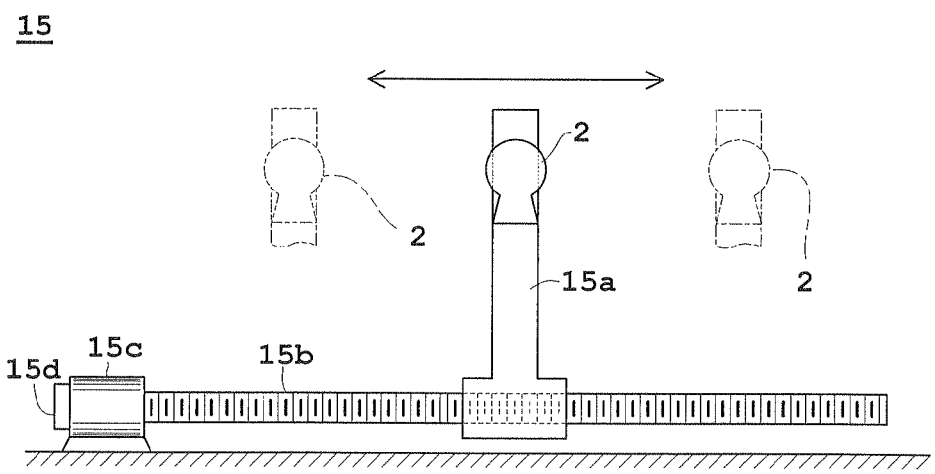
FIG. 3 is a schematic view showing an outline of an X-ray tube driver relating to driving of an X-ray tube.

2 . . . X-ray tube
3 . . . flat panel X-ray detector (FPD)
13 . . . monitor
9a . . . correcting unit
9b . . . image decomposing unit
9c . . . image composing unit
9d . . . reconstruction processing unit
d . . . pitch
z . . . body axis
M . . . patient Embodiment An embodiment of this invention will be described hereinafter with reference to the drawings. FIG. 1 is a block diagram of an X-ray tomography apparatus according to the embodiment. FIG. 2 is a schematic view showing an outline of an FPD drive mechanism relating to driving of a flat panel X-ray detector. FIG. 3 is a schematic view showing an outline of an X-ray tube driver relating to driving of an X-ray tube. This embodiment will be described, taking the flat panel X-ray detector (hereinafter abbreviated as "FPD") as an example of radiation detecting device, and the X-ray tomography apparatus as an example of radiographic apparatus.

As shown in FIG. 1, the X-ray tomography apparatus includes a top board 1 for supporting a patient M, an X-ray tube 2 for emitting X-rays toward the patient M, and an FPD 3 for detecting X-rays transmitted through the patient M. The X-ray tube 2 corresponds to the radiation emitting device in this invention. The FPD 3 corresponds to the radiation detecting device in this invention.

The X-ray tomography apparatus further includes a top board controller 4 for controlling vertical and horizontal movements of the top board 1, an FPD controller 5 for controlling scanning action of the FPD 3, an X-ray tube controller 7 having a high voltage generator 6 for generating a tube voltage and tube current for the X-ray tube 2, an analog-to-digital converter 8 for digitizing and fetching X-ray detection signals which are charge signals from the FPD 3, an image processor 9 for performing various processes based on the X-ray detection signals outputted from the analog-to-digital converter 8, a controller 10 for performing an overall control of these components, a memory 11 for storing processed images, an input unit 12 for the operator to input various settings, and a monitor 13 for displaying the processed images and other information. The monitor 13 corresponds to the output device in this invention.

The top board controller 4 controls movement of the top board 1, such as moving the top board 1 horizontally to place the patient M in an imaging position, vertically moving and/or rotating the top board 1 to set the patient M to a desired position, horizontally moving the top board 1 during an imaging operation, and horizontally moving the top board 1 to withdraw the patient M from the imaging position after the imaging operation. These controls are carried out by controlling a top board driving mechanism (not shown) including motors and encoders (not shown).

The FPD controller 5 controls the FPD 3 to make parallel translation along the direction of a body axis z which is a longitudinal direction of the patient M. As shown in FIG. 2, this control is carried out by controlling an FPD drive mechanism 14 including a rack 14$a$, a pinion 14$b$, a motor 14$c$ and an encoder 14$d$. Specifically, the rack 14$a$ extends along the direction of body axis z of the patient M. The pinion 14$b$ supports the FPD 3, is in part meshed with the rack 14$a$, and is rotatable by rotation of the motor 14$c$. For example, when the motor 14$c$ is rotated forward, the FPD 3 will make parallel translation along the rack 14$a$ toward the feet of the patient M as shown in the alternate long and short dash line in FIG. 2. When the motor 14$c$ is reversed, the FPD 3 will make parallel translation along the rack 14$a$ toward the head of the patient M as shown in the two-dot chain line in FIG. 2. The encoder 14$d$ detects a direction of rotation and an amount of rotation of the motor 14$c$ corresponding to a direction of movement and an amount of movement (moving distance) of the FPD 3. Results of detection by the encoder 14$d$ are sent to the FPD controller 5.

The high voltage generator 6 generates the tube voltage and tube current for application to the X-ray tube 2 to emit X-rays. The X-ray tube controller 7 controls the X-ray tube 2 to make parallel translation along the direction of body axis z of the patient M. As shown in FIG. 3, this control is carried out by controlling an X-ray tube driver 15 including a strut 15$a$, a threaded rod 15$b$, a motor 15$c$ and an encoder 15$d$. Specifically, the strut 15$a$ carries and supports the X-ray tube 2 on an upper end portion thereof, and is screwed to the threaded rod 15$b$ at a lower end portion. The threaded rod 15$b$ extends along the direction of body axis z of the patient M and is rotatable by rotation of the motor 15$c$. For example, when the motor 15$c$ is rotated forward, the X-ray tube 2 will make parallel translation with the strut 15$a$ toward the feet of the patient M as shown in the alternate long and short dash line in FIG. 3. When the motor 15$c$ is reversed, the X-ray tube 2 will make parallel translation with the strut 15$a$ toward the head of the patient M as shown in the two-dot chain line in FIG. 3. The encoder 15$d$ detects a direction of rotation and an amount of rotation of the motor 15$c$ corresponding to a direction of movement and an amount of movement (moving distance) of the X-ray tube 2. Results of detection by the encoder 15$d$ are sent to the X-ray tube controller 7.

In order that the X-ray tube 2 and FPD 3 make parallel translation in the same direction along the direction of body axis z of the patient M as shown in FIG. 1, the FPD controller 5 and X-ray tube controller 7 carry out controls so that the direction of rotation of the motor 14$c$ in FIG. 2 and the direction of rotation of the motor 15$c$ in FIG. 3 may be the same. In this embodiment, it is preferred that the X-ray tube 2 and FPD 3 make parallel translation at an equal speed. That is, the FPD controller 5 controls the amount of rotation of the motor 14$c$ and the X-ray tube controller 7 controls the amount of rotation of the motor 15$c$, so that the amount of movement of the X-ray tube 2 and the amount of movement of the FPD 3 may be the same.

The X-ray tube controller 7 controls also setting of an irradiation field of a collimator (not shown) adjacent the X-ray tube 2. In this embodiment, an irradiation field is set by controlling the collimator to emit X-rays in a fan beam form diverging in the longitudinal direction (the direction of body axis z) and the transverse direction (direction perpendicular in a horizontal plane to the body axis z) of the patient M. The X-ray tube controller 7 controls the X-ray tube 2 to emit X-rays (in the fan beam form) intermittently whenever the X-ray tube 2 and FPD 3 move every pitch (predetermined distance) described hereinafter. The FPD controller 5 controls the FPD 3 to detect X-rays transmitted through the patient M irradiated intermittently.

The controller 10 has a central processing unit (CPU) and other elements. The memory 11 has storage media, typically a ROM (Read-Only Memory) and RAM (Random Access Memory). The input unit 12 has a pointing device, typically a mouse, keyboard, joy stick, trackball and/or touch panel.

The image processor 9 includes a correcting unit 9$a$ for carrying out lag correction and gain correction on the X-ray detection signals, carrying out corrections in FIG. 8 to be described hereinafter, and outputting X-ray images projected on the detecting plane of FPD 3, an image decomposing unit 9$b$ for decomposing the corrected X-ray images for every pitch, an image composing unit 9$c$ for composing the decomposed images for each projection angle to obtain a projection image for each projection angle, and a reconstruction processing unit 9$d$ for carrying out a reconstruction process based on the composed projection images to obtain a sectional image. The correcting unit 9$a$ corresponds to the correcting device in this invention. The image decomposing unit 9$b$ corresponds to the image decomposing device in this invention. The image composing unit 9$c$ corresponds to the image composing device in this invention. The reconstruction processing unit 9$d$ corresponds to the reconstruction processing device in this invention. Specific functions of the correcting unit 9$a$ and image decomposing unit 9$b$ will be described hereinafter with reference to FIGS. 6-8. Specific functions of the image composing unit 9$c$ and reconstruction processing unit 9$d$ will be described hereinafter with reference to FIGS. 9 and 10.

The memory 11 is constructed for writing and storing each image processed by the image processor 9. As does the controller 10, the FPD controller 5 and X-ray tube controller 7 also have CPUs and so on.

Figure 4:
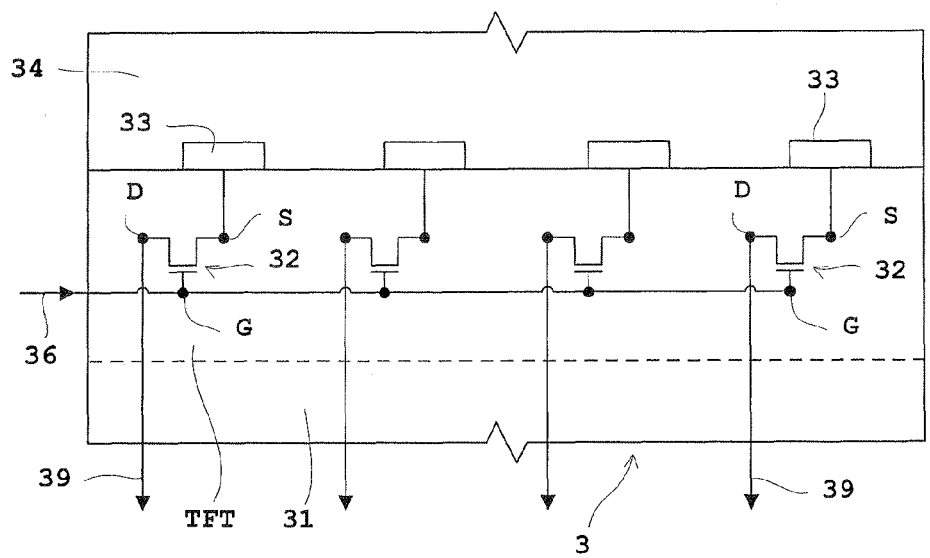
FIG. 4 is an equivalent circuit, seen in side view, of the flat panel X-ray detector (FPD)
Figure 5:
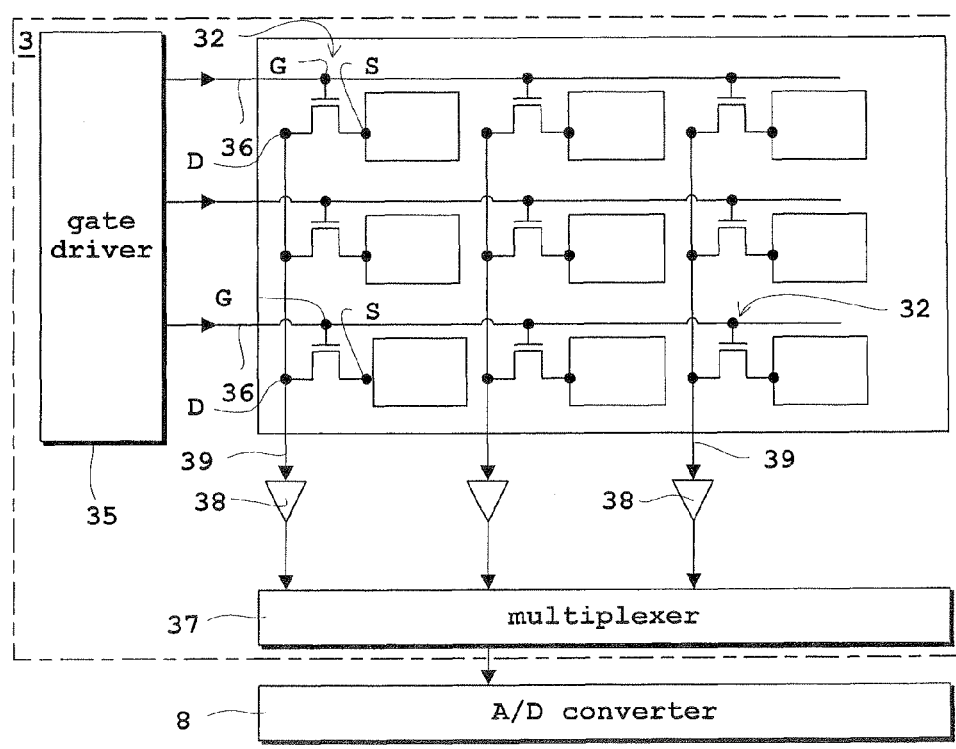
FIG. 5 is an equivalent circuit, seen in plan view, of the flat panel X-ray detector (FPD)

Next, the construction of the flat panel X-ray detector (FPD) 3 will be described with reference to FIGS. 4 and 5. FIG. 4 is an equivalent circuit, seen in side view, of the flat panel X-ray detector (FPD). FIG. 5 is an equivalent circuit, seen in plan view, of the flat panel X-ray detector (FPD).

As shown in FIG. 4, the FPD 3 includes a glass substrate 31, and thin film transistors TFT formed on the glass substrate 31. As shown in FIGS. 4 and 5, the thin film transistors TFT comprise numerous (e.g. 1,024×1,024) switching elements 32 arranged in a two-dimensional matrix of rows and columns. The switching elements 32 are formed separate from one another for respective carrier collecting electrodes 33. Thus, the FPD 3 is also a two-dimensional array radiation detector.

As shown in FIG. 4, an X-ray sensitive semiconductor 34 is laminated on the carrier collecting electrodes 33. As shown in FIGS. 4 and 5, the carrier collecting electrodes 33 are connected to the sources S of the switching elements 32. A plurality of gate bus lines 36 extend from a gate driver 35, and are connected to the gates G of the switching elements 32. On the other hand, as shown in FIG. 5, a plurality of data bus lines 39 are connected through amplifiers 38 to a multiplexer 37 for collecting charge signals and outputting as one. As shown in FIGS. 4 and 5, each data bus line 39 is connected to the drains D of the switching elements 32.

With a bias voltage applied to a common electrode not shown, the gates of the switching elements 32 are turned on by applying thereto (or reducing to 0V) the voltage of the gate bus lines 36. The carrier collecting electrodes 33 output charge signals (carriers) converted from X-rays incident on the detecting plane through the X-ray sensitive semiconductor 34, to the data bus lines 39 through the sources S and drains D of the switching elements 32. The charge signals are provisionally stored in capacitors (not shown) until the switching elements are turned on. The amplifiers 38 amplify the charge signals read out to the data bus lines 39, and the multiplexer 37 collects the charge signals, and outputs them as one charge signal. The analog-to-digital converter 8 digitizes the outputted charge signals, and outputs them as X-ray detection signals.

Figure 6:
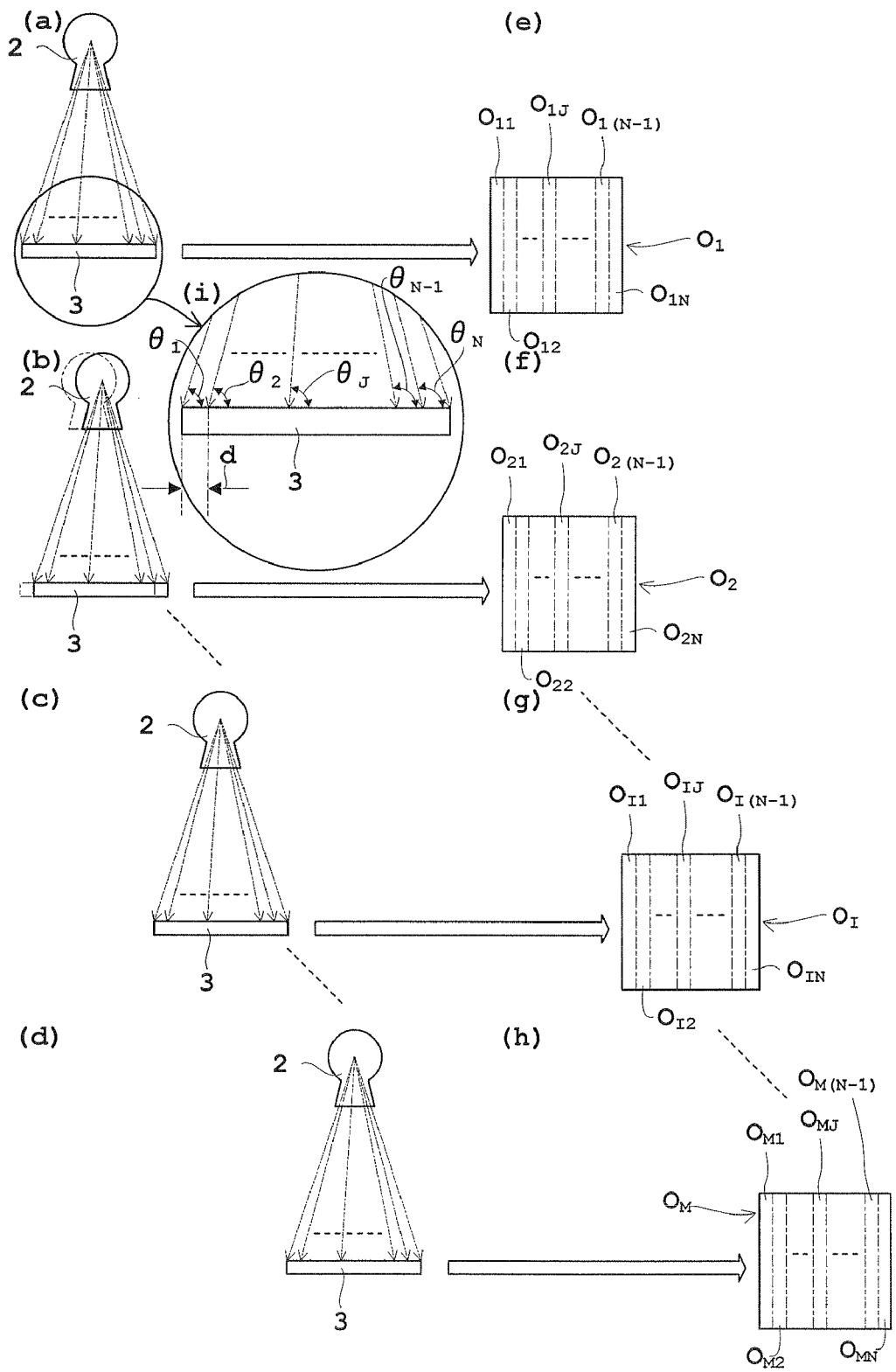
FIG. 6 (a)-(i) are schematic views depicting for each pitch (predetermined distance) an image pickup principle by the X-ray tube and flat panel X-ray detector (FPD)
Figure 7:
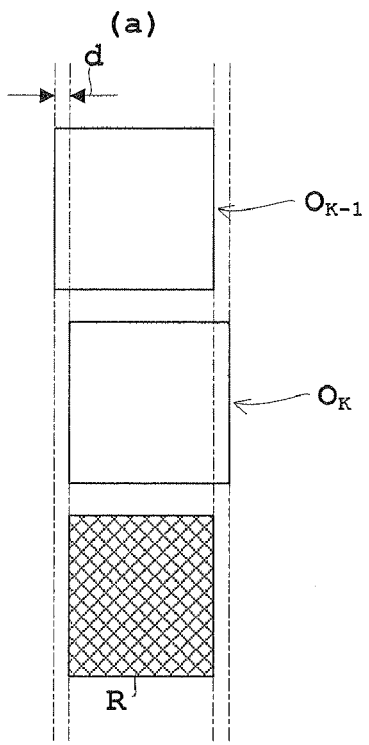
FIGS. 7 (a), (b) are schematic explanatory views of overlapping areas of X-ray images between frames adjoining each other in time.
Figure 7:
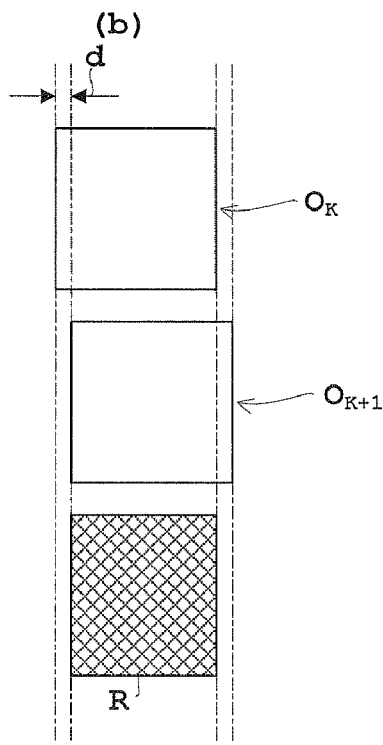

Next, specific functions of the correcting unit 9a and image decomposing unit 9b will be described with reference to FIGS. 6-8. FIG. 6 is a schematic view depicting for every pitch (predetermined distance) an image pickup principle by the X-ray tube and flat panel X-ray detector (FPD). FIG. 7 is a schematic explanatory view of overlapping areas of X-ray images between frames adjoining each other in time. FIG. 8 is a flow chart of a series of corrections according to the embodiment. Description will be made assuming that X-ray images projected on the detecting plane of FPD 3 have already gone through the processes of lag correction and gain correction by the correcting unit 9a.

X-ray images projected on the detecting plane of FPD 3, as the X-ray tube 2 and FPD 3 move every pitch d, as shown in FIGS. 6(a)-6(d), are referred to as $O_1, O_2, \ldots, O_I, \ldots,$ and $O_M$ as shown in FIGS. 6(e)-6(h) ($1 \leq I \leq M$). Whenever the X-ray tube 2 and FPD 3 move every pitch d, the X-ray tube 2 emits X-rays intermittently. That is, with movement by every pitch d, X-rays are emitted in pulse.

Specifically, when X-rays are first emitted with the X-ray tube 2 and FPD 3 located in the position shown in FIG. 6(a), X-rays are next emitted in the position shown in FIG. 6(b) after movement by pitch d. The FPD 3 detects the X-rays in FIG. 6(a), to obtain X-ray image $O_1$ (see FIG. 6(e)). The FPD 3 detects X-rays in FIG. 6(b), to obtain X-ray image $O_2$ (see FIG. 6(f)). Similarly thereafter, as the X-ray tube 2 and FPD 3 move every pitch d, X-rays are emitted for the (I−1)th time in the position shown in FIG. 6(c), and the FPD 3 detects the X-rays in FIG. 6(c), to obtain X-ray image $O_I$ (see FIG. 6(g)). Finally, X-rays are emitted for the (M−1)th in the position shown in FIG. 6(d), and the FPD 3 detects the X-rays in FIG. 6(d), to obtain X-ray image $O_M$ (see FIG. 6(h)). In this embodiment, the image pickup start position in FIG. 6(a) is the head of the patient M, the image pickup end position in FIG. 6(d) is the feet of the patient M, and movement is made in order from the head to the feet with the movement of the X-ray tube 2 and FPD 3 as in FIGS. 6(a)-6(d).

With the X-ray tube 2 and FPD 3 moving every pitch d, the image decomposing unit 9b can decompose X-ray images $O_1, O_2, \ldots, O_I, \ldots,$ and $O_M$ at every pitch d. Specifically, as shown in the enlarged view of FIG. 6(i), projection angles which are angles between the radiation axis from the X-ray tube 2 to the FPD 3 and the body axis z of the patient are referred to as $\theta_1, \theta_2, \ldots, \theta_J, \ldots, \theta_{N-1}$ and $\theta_N$ for every pitch d ($1 \leq J \leq N$). Then, the images decomposed at every pitch d coincide with images divided into the same projection angles $\theta_1, \theta_2, \ldots, \theta_J, \ldots, O_{N-1},$ and $\theta_N$, respectively.

As shown in FIG. 6(e), X-ray image $\theta_1$ is decomposed at every pitch d into $O_{11}, O_{12}, \ldots, O_{1J}, \ldots, O_{1(N-1)}$ and $O_{1N}$. Decomposed image $O_{11}$ is an image obtained from an emission at projection angle $\theta_1$. Decomposed image $O_{12}$ is an image obtained from an emission at projection angle $\theta_2$. Similarly thereafter, decomposed image $O_{1J}$ is an image obtained from an emission at projection angle $\theta_J$. Finally, decomposed image $O_{1N}$ is an image obtained from an emission at projection angle $\theta_N$.

Similarly, as shown in FIG. 6(f), X-ray image $O_2$ is decomposed at every pitch d into $O_{21}, O_{22}, \ldots, O_{2J}, \ldots, O_{2(N-1)}$ and $O_{2N}$. Decomposed image $O_{21}$ is an image obtained from the emission at projection angle $\theta_1$. Decomposed image $O_{22}$ is an image obtained from the emission at projection angle $\theta_2$. Similarly thereafter, decomposed image $O_{2J}$ is an image obtained from the emission at projection angle $\theta_2$. Finally, decomposed image $O_{2N}$ is an image obtained from the emission at projection angle $\theta_N$.

At the (I−1)th time, as shown in FIG. 6(g), X-ray image $O_I$ is decomposed at every pitch d into $O_{I1}, O_{I2}, \ldots, O_{IJ}, \ldots, O_{I(N-1)}$ and $O_{IN}$. Decomposed image $O_{I1}$ is an image obtained from the emission at projection angle $\theta_1$. Decomposed image $O_{I2}$ is an image obtained from the emission at projection angle $\theta_2$. Similarly thereafter, decomposed image $O_{IJ}$ is an image obtained from the emission at projection angle $\theta_J$. Finally, decomposed image $O_{IN}$ is an image obtained from the emission at projection angle $\theta_N$.

Finally, at the (M−1)th time, as shown in FIG. 6(h), X-ray image $O_I$ is decomposed at every pitch d into $O_{M1}, O_{M2}, \ldots, O_{MJ}, \ldots, O_{M(N-1)}$ and $O_{MN}$. Decomposed image $O_{M1}$ is an image obtained from the emission at projection angle $\theta_1$. Decomposed image $O_{M2}$ is an image obtained from the emission at projection angle $\theta_2$. Similarly thereafter, decomposed image $O_{MJ}$ is an image obtained from the emission at projection angle $\theta_J$. Finally, decomposed image $O_{MN}$ is an image obtained from the emission at projection angle $\theta_N$.

Before carrying out such decomposition, each of the X-ray images $O_1, O_2, \ldots, O_I, \ldots,$ and $O_M$ is corrected. The X-ray image in the first frame 1 is $O_1$, and the X-ray image in the second frame 2 $O_2$. The X-ray image in the last frame is regarded as $O_M$. That is, the last frame is regarded as frame M. As shown in FIG. 7(a), of X-ray images $O_{K-1}$ and $O_K$ in two, frame (K−1) and frame K adjoining each other in time, where K is a natural number, the correcting unit 9a corrects one X-ray image based on the other X-ray image.

Assuming that X-ray images $O_{K-1}$ and $O_K$ in two, frame (K−1) and frame K+1 have overlapping areas R, the overlapping areas R correspond to an area shown in cross hatching in FIG. 7(a). Similarly, overlapping areas R of X-ray images $O_K$ and $O_{K+1}$ in two, frame K and frame (K+1) adjoining each other in time correspond to an area shown in cross hatching in FIG. 7(b). The overlapping areas R can be regarded as nearly identical images although there is a difference resulting from a slight difference in projection angle.

Figure 8:
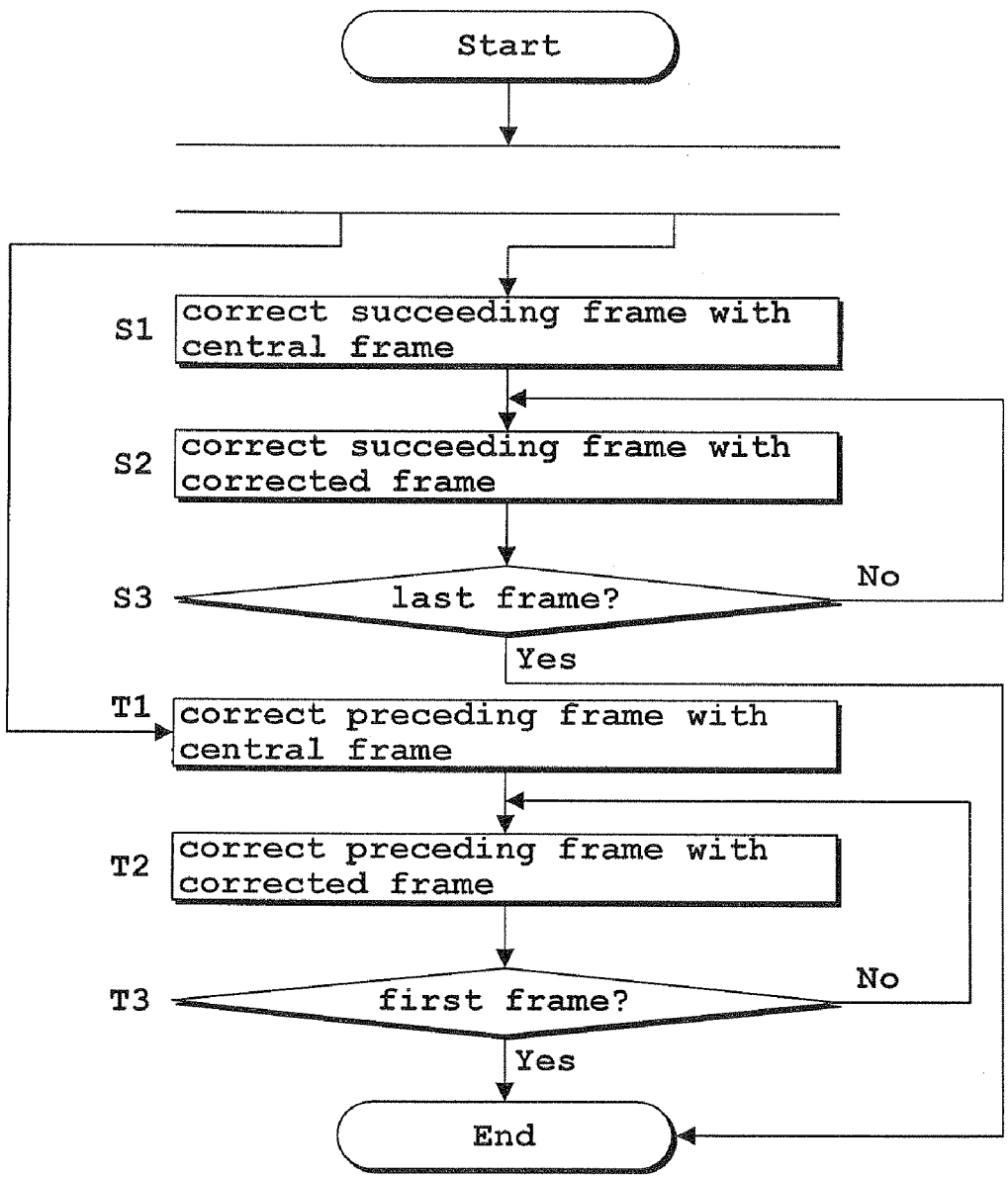
FIG. 8 is a flow chart of a series of corrections according to the embodiment.

In making corrections using the X-ray image in two, frame K and frame (K+1) (or frame (K−1) and frame K) adjoining each other in this way, the correcting unit 9a carries out the corrections through the flow shown in FIG. 8. When M is an odd number, an X-ray image serving as a reference for correction is determined so as to satisfy K=(M+1)/2. When M is an even number, an X-ray image serving as a reference for correction is determined so as to satisfy K=M/2+1 or K=M/2. In this embodiment, in order to finish the correction of X-ray image $O_M$ in the last frame M and the correction of X-ray image $O_1$ in the first frame 1 at the same time, description will be made of an example where M is an even number, and step S1 and step T1 in FIG. 8 are carried out in parallel. At this time, since X-ray image OK in frame K which satisfies K=(M+1)/2 is at the center in time, this X-ray image OK is called the X-ray image in the central frame.

(Step S1) Correct Succeeding Frame with Central Frame

Excluding the X-ray images in the first frame 1 and the last frame M, based on one X-ray image $O_K$ in frame K which is the frame preceding in time (i.e. X-ray image $O_K$ in the central frame) of the X-ray images in two, frame K and frame (K+1) adjoining each other in time, the other X-ray image $O_{K+1}$ in frame (K+1) which is the frame succeeding in time is corrected. Specifically, although a difference in pixel value (i.e. a luminance difference) occurs between X-ray image $O_K$ and X-ray image $O_{K+1}$, X-ray image $O_{K+1}$ which is the target of correction is corrected for the overlapping area R to reduce the luminance difference.

As the simplest technique, the pixel values of X-ray image $O_{K+1}$ in the overlapping area R may be replaced with the pixel values of X-ray image $O_K$ in the overlapping area R on a pixel-by-pixel basis. X-ray image $O_{K+1}$ can be corrected through such replacing operation to reduce the luminance difference in the overlapping area R to "0". As another technique, in order to place some importance on image characteristics of X-ray image $O_{K+1}$ itself, for example, the difference in pixel value between X-ray image $O_K$ and X-ray image $O_{K+1}$ may be multiplied by a constant less than 1, and a value obtained by the multiplication may be added to the pixel values of X-ray image $O_{K+1}$ in the overlapping area R.

(Step S2) Correct Succeeding Frame with Corrected Frame

Based on a corrected one of the X-ray images which is the frame preceding in time of the X-ray images in two frames adjoining each other in time and including, in the frame preceding in time, the X-ray image $O_{K+1}$ corrected in step S1 or the X-ray image corrected in this step S2 (X-ray image in the corrected frame), the other X-ray frame which is the frame succeeding in time is corrected. A specific correcting technique is the same as described in step S1, and its description is omitted.

(Step S3) Last Frame?

A determination is made whether the X-ray image in the frame which is the target of correction is X-ray image $O_M$ in the last frame M. When it is not the last frame M, noting that the correction is not completed for the X-ray image in each frame following X-ray image $O_K$ in the central frame, the operation returns to step S2 to carry out a similar correction. That is, step S2 is repeated until X-ray image $O_M$ in the last frame M is corrected. When it is the last frame M, noting that the correction is completed for the X-ray image in each frame following X-ray image $O_K$ in the central frame, a series of corrections is ended and the corrected X-ray images are decomposed.

(Step T1) Correct Preceding Frame with Central Frame

The process in step T1 is carried out in parallel with the process in step S1. Excluding the X-ray images in the first frame 1 and the last frame M, based on one X-ray image $O_K$ in frame K which is the frame succeeding in time (i.e. X-ray image $O_K$ in the central frame) of the X-ray images in two, frame (K−1) and frame K adjoining each other in time, the other X-ray image $O_{K−1}$ in frame (K−1) which is the frame preceding in time is corrected. A specific correcting technique is the same as described in step S1, and its description is omitted.

(Step T2) Correct Preceding Frame with Corrected Frame

Based on a corrected one of the X-ray images which is the frame succeeding in time of the X-ray images in two frames adjoining each other in time and including, in the frame succeeding in time, the X-ray image $O_{K−1}$ corrected in step T1 or the X-ray image corrected in this step T2 (X-ray image in the corrected frame), the other X-ray frame which is the frame preceding in time is corrected. A specific correcting technique is the same as described in step S1, and its description is omitted.

(Step T3) First Frame?

A determination is made whether the X-ray image in the frame which is the target of correction is X-ray image $O_1$ in the first frame 1. When it is not the first frame 1, noting that the correction is not completed for the X-ray image in each frame preceding X-ray image $O_K$ in the central frame, the operation returns to step T2 to carry out a similar correction. That is, step T2 is repeated until X-ray image $O_1$ in X-ray image $O_1$ in the first frame 1 is corrected. When it is the first frame 1, noting that the correction is completed for the X-ray image in each frame preceding X-ray image $O_K$ in the central frame, a series of corrections is ended and the corrected X-ray images are decomposed.

Figure 9:
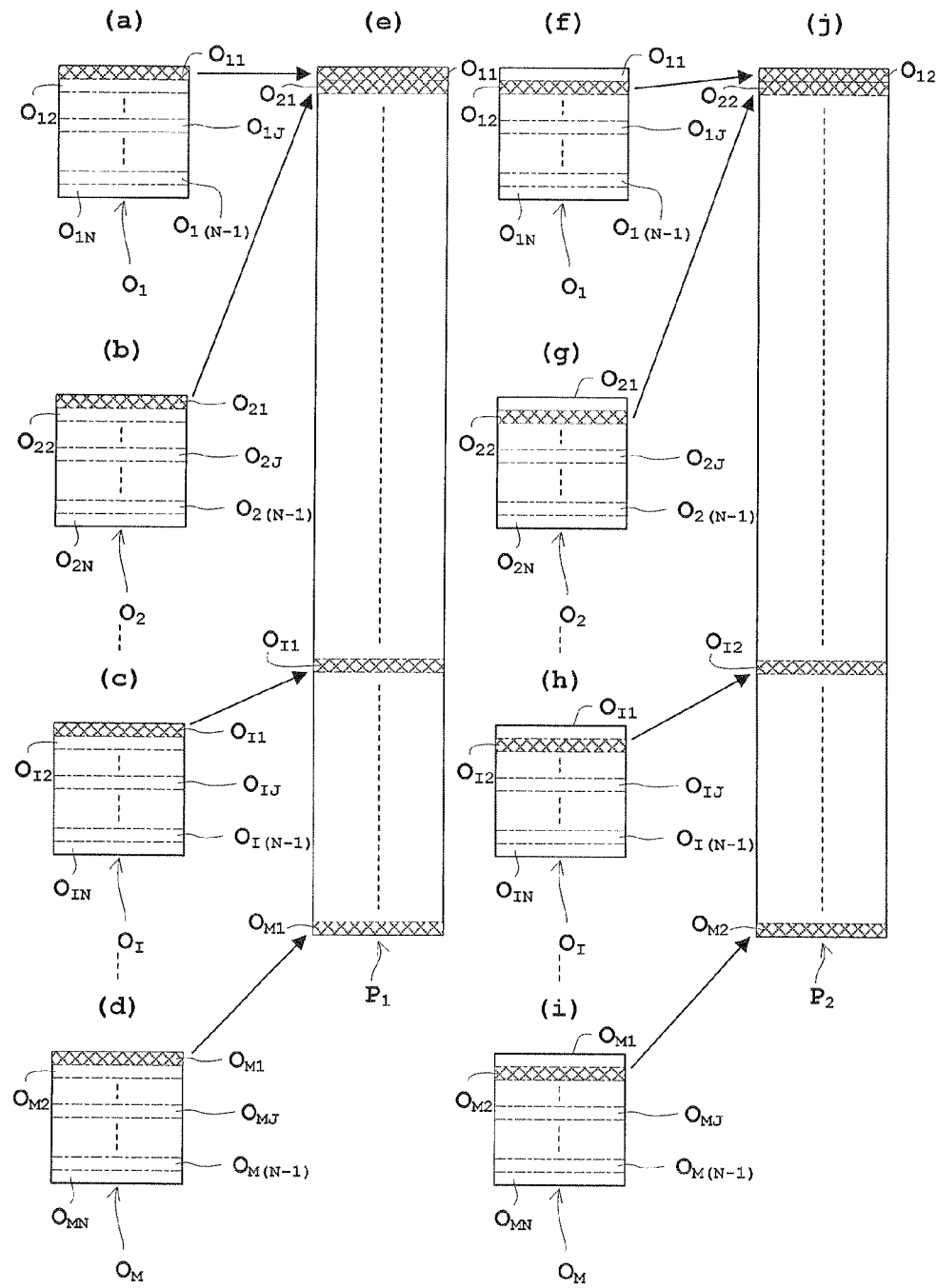
FIG. 9 (a)-(j) are schematic views depicting separation of images and composition for projection images.
Figure 10:
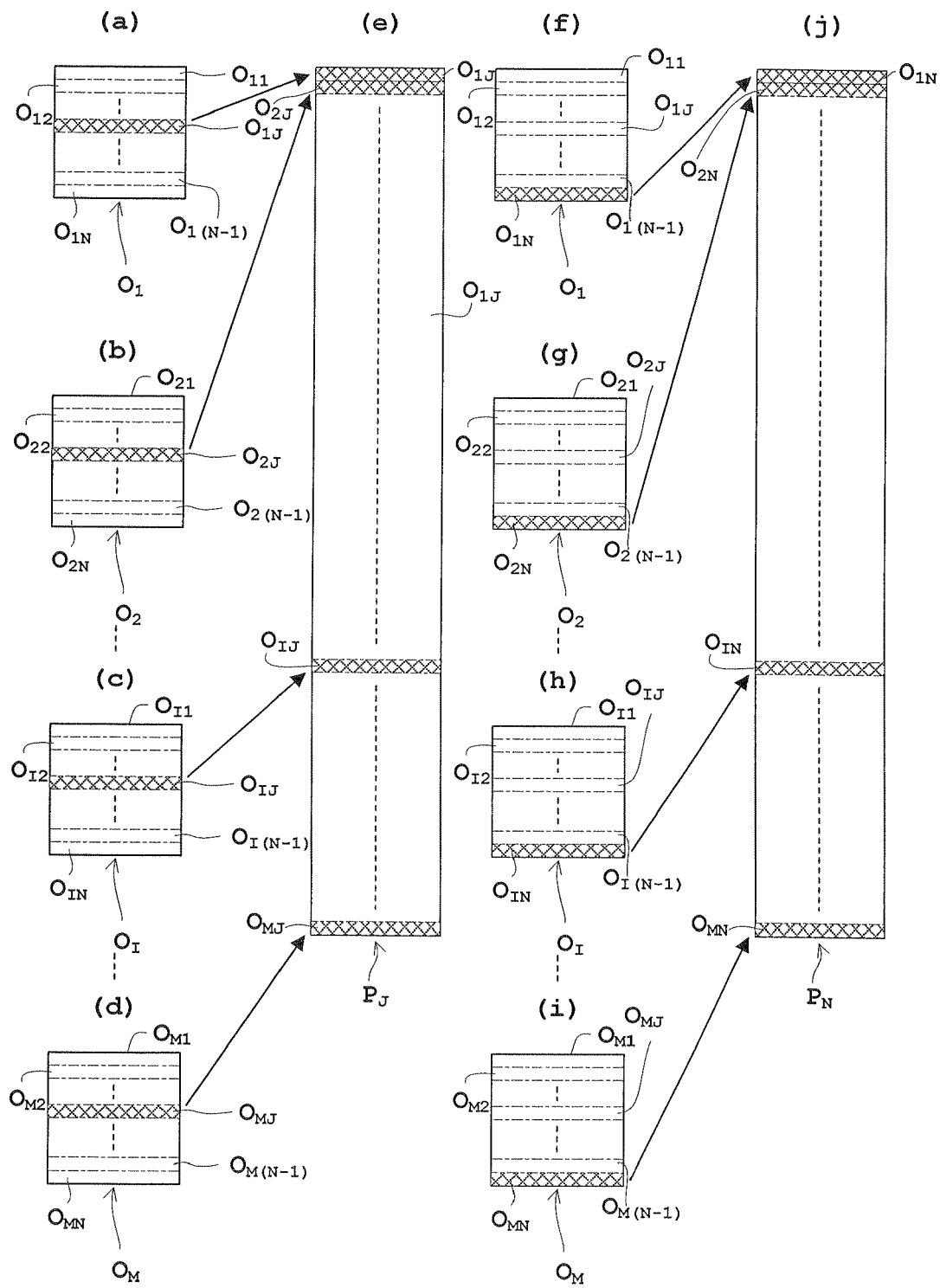
FIG. 10 (a)-(j) are schematic views depicting separation of images and composition for projection images.
Figure 11:
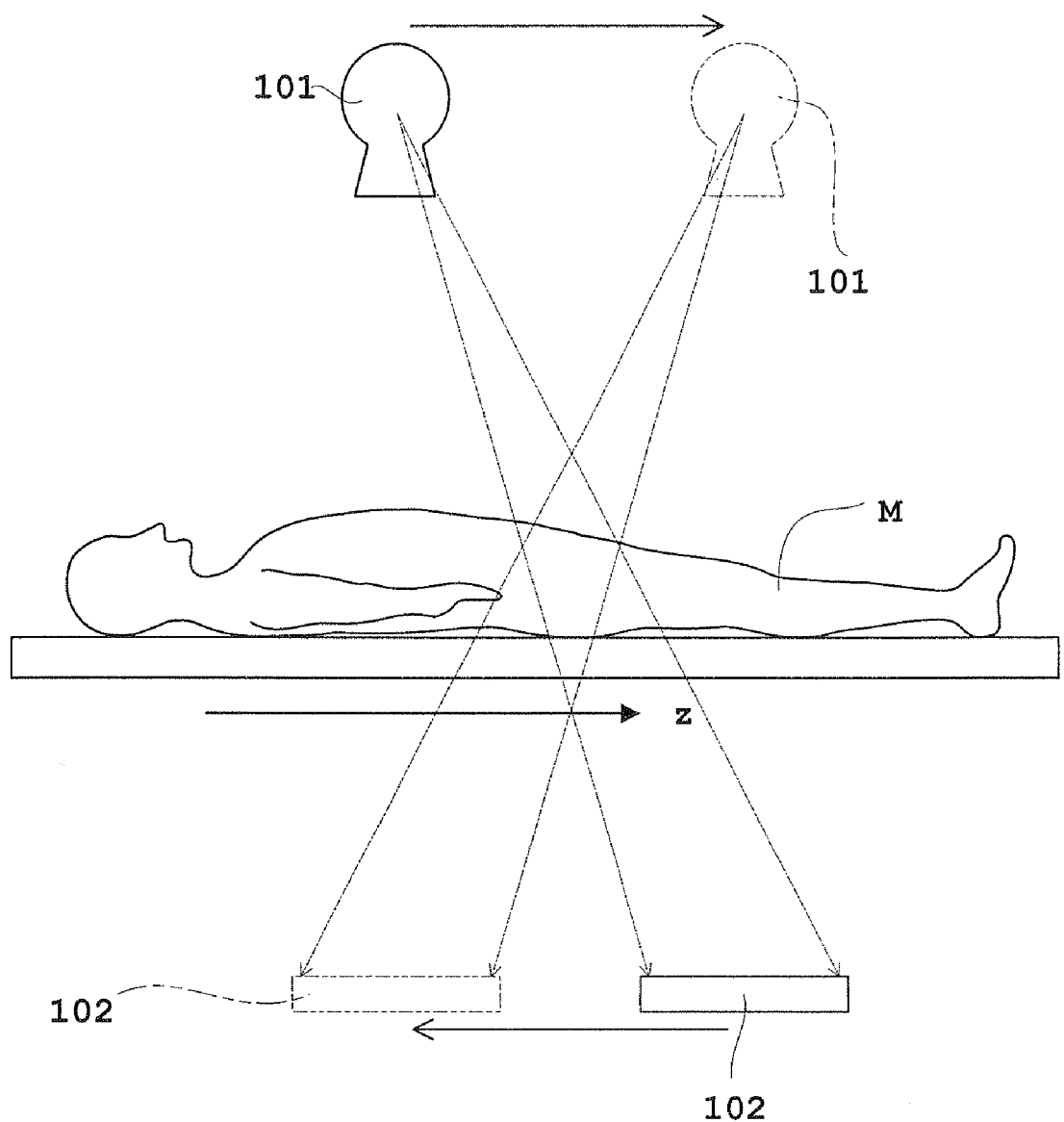
FIG. 11 is a side view showing an outline of a conventional X-ray tomography apparatus.

Next, specific functions of the image composing unit 9c and reconstruction processing unit 9d will be described with reference to FIGS. 9 and 10. FIGS. 9 and 10 are schematic views depicting separation of images and composition for projection images. The X-ray images corrected in steps S1-S3 and T1-T3 are decomposed as described in FIG. 6 also. The image composing unit 9c composes the images decomposed in this way, for each of the same projection angles $\theta_1$, $\theta_2$, ..., $\theta_J$, ..., $\theta_{N-1}$ and $\theta_N$ as shown in FIGS. 9 and 10. The respective X-ray images $O_1$, $O_2$, ..., $O_J$, ..., and $O_M$ corrected as described above have decomposed images (that is, divided into the projection angles $\theta_1$, $\theta_2$, ..., $\theta_J$, ..., $\theta_{N-1}$ and $\theta_N$) for each pit d as shown in FIGS. 9(a)-9(d), FIGS. 9(f)-9(i), FIGS. 10(a)-10(d), and FIGS. 10(f)-10(i).

In the case of projection angle $\theta_1$, for example, image $O_{11}$ in X-ray image $O_1$ shown in FIG. 9(a), image $O_{21}$ in X-ray image $O_2$ shown in FIG. 9(b), ..., image $O_{J1}$ in X-ray image $O_J$ shown in FIG. 9(c), ..., and image $O_{M1}$ in X-ray image $O_M$ shown in FIG. 9(d) are composed to obtain projection image $P_1$ for projection angle $\theta_1$ as shown in FIG. 9(e).

Similarly, in the case of projection angle $\theta_2$, image $O_{12}$ in X-ray image $O_1$ shown in FIG. 9(f), image $O_{22}$ in X-ray image $O_2$ shown in FIG. 9(g), ..., image $O_{J2}$ in X-ray image $O_J$ shown in FIG. 9(h), ..., and image $O_{M2}$ in X-ray image $O_M$ shown in FIG. 9(i) are composed to obtain projection image $P_2$ for projection angle $\theta_2$ as shown in FIG. 9(j).

At the (J−1)th time, in the case of projection angle $O_J$, image $O_{1J}$ in X-ray image $O_1$ shown in FIG. 10(a), image $O_{2J}$ in X-ray image $O_2$ shown in FIG. 10(b), image $O_{IJ}$ in X-ray image $O_I$ shown in FIG. 10(c), ..., and image $O_{MJ}$ in X-ray image $O_M$ shown in FIG. 10(d) are composed to obtain projection image $P_J$ for projection angle $\theta_J$ as shown in FIG. 10(e).

Finally, at the (N−1)th time, in the case of projection angle $\theta_N$, image $O_{1N}$ in X-ray image $O_1$ shown in FIG. 10(f), image $O_{2N}$ in X-ray image $O_2$ shown in FIG. 10(g), ..., image $O_{IN}$ in X-ray image $O_I$ shown in FIG. 10(h), ..., and image $O_{MN}$ in X-ray image $O_M$ shown in FIG. 10(i) are composed to obtain projection image $P_N$ for projection angle $\theta_N$ as shown in FIG. 10(j).

To summarize the above, the image composing unit 9c composes the decomposed images for each of the same projection angles $\theta_1$, $\theta_2$, ..., $\theta_J$, ..., $\theta_{N-1}$ and $\theta_N$ to obtain projection images $P_1$, $P_2$, ..., $P_J$, ..., and $P_N$ for the respective projection angles $\theta_1$, $\theta_2$, ..., $\theta_J$, ..., $\theta_{N-1}$ and $\theta_N$ as shown in FIGS. 9(e), 9(j), 10(e) and 10(j).

The reconstruction processing unit 9d carries out a reconstruction process based on the composed projection images $P_1, P_2, \ldots, P_J, \ldots$, and $P_N$ to obtain a sectional image. The reconstruction process may be carried out using the well-known filtered back projection (FBP) (also called "filter-corrected back projection").

Where the number of projection images $P_1, P_2, \ldots, P_J, \ldots$, and $P_N$ is N [Frames], the moving speed of the imaging system such as the X-ray tube 2 and FPD 3 is v [mm/sec], the view size of FPD 3 is V[mm], and the image pickup cycle (called "pulse time width") is T [sec/Frame], the moving speed v [ram/sec] is expressed by v[mm/sec]=V [mm]/N[Frame]×1/T [sec/Frame]. The inverse of the image pickup cycle is image pickup speed, and where the image pickup speed is F [Frame/sec], the moving speed v [mm/sec] is expressed also by v[mm/sec]=V[mm]/N[Frame]×F [Frame/sec]. Pitch d [mm] is expressed by d [mm]=V[mm]/N [Frames].

Where, for example, view size V used in this embodiment is 17 inches (=430 [mm]), the number N of projection images $P_1, P_2, \ldots, P_J, \ldots$, and $P_N$ is 50 [Frames], and the image pickup speed F is 15 [Frames/sec], the moving speed v is v=[mm/sec]=430 [mm]/50[Frames]×15 [Frames/sec]=129 [mm/sec], and pitch d is 430 [mm]/50 [Frames]=8.6 [mm/Frame]. Therefore, the X-ray tube 2 and FPD 3 are moved parallel to each other at the same speed of 129 [mm/sec], and X rays are emitted intermittently with the timing of image pickup speed 15 [Frame/sec], whereby X rays are emitted intermittently from the X-ray tube 2 as the X-ray tube 2 and FPD 3 move every pitch 8.6 [mm/Frame]. And 50 projection images $P_1, P_2, \ldots, P_J, \ldots$, and $P_{50}$ can be obtained. Further, the longer distance the X-ray tube 2 and FPD 3 move, the longer becomes the area of each of the projection images $P_1, P_2, \ldots, P_J, \ldots$, and $P_N$ as shown in FIGS. 9 and 10.

According to the X-ray tomography apparatus in this embodiment, data of a long field of view of the body axis z which is the longitudinal direction can be obtained from the FPD 3 by constructing that the X-ray tube 2 and flat panel X-ray detector (FPD) 3 are movable parallel to each other in the same direction along the body axis z which is the longitudinal direction of the patient M. On the other hand, whenever the X-ray tube 2 and FPD 3 move every pitch (predetermined distance), X-rays are intermittently emitted from the X-ray tube 2, and the FPD 3 detects X-rays transmitted through the patient M intermittently irradiated. And the image decomposing unit 9b decomposes the X-ray images for every pitch noted above. The image composing unit 9c composes the decomposed images for each of the same projection angles to obtain projection images for each projection angle. Therefore, the reconstruction processing unit 9d can obtain a sectional image having a long field of view in the longitudinal direction by carrying out a reconstruction process based on the composed projection images.

The image decomposing unit 9b, image composing unit 9c and reconstruction processing unit 9d are the technique described in the paragraphs "Problem to Be Solved by the Invention". This embodiment provides the following construction before the image decomposing unit 9b decomposes X-ray images for every pitch. That is, the correcting unit 9a corrects X-ray images based on overlapping areas of a plurality of X-ray images based on X-ray detection signals detected whenever a movement is made in the same direction. The areas used in this correction are areas having strong correlativity, and since the correction is made taking such areas into consideration, luminance differences among different X-ray images can be reduced. And the image decomposing unit 9b decomposes such corrected X-ray images for every pitch. The image composing unit 9c composes the decomposed images for each of the same projection angles to obtain a projection image for each projection angle. The reconstruction processing unit 9d carries out a reconstruction process based on the composed projection images, thereby obtaining sectional images with a long field of view in the longitudinal direction while reducing the luminance differences among the different X-ray images.

In this embodiment, when K is a natural number, of X-ray images in two, frame K and frame (K+1) adjoining each other in time, the correcting unit 9a corrects one X-ray image based on the other X-ray image (steps S1 and T1 in FIG. 8). The luminance difference between the frames can be reduced by the correction using the X-ray images in such two, frame K and frame (K+1) adjoining each other in time.

In this embodiment, when a correction is made using the X-ray images in two, frame K and frame (K+1) adjoining each other in time, of the X-ray images in two frames adjoining each other in time, including a corrected frame, the correcting unit 9a repeats the procedure of correcting one X-ray image based on the other, above-noted corrected X-ray image (steps S2-S3 and T2-T3 in FIG. 8). Through such correction, the luminance difference between frames can be reduced in an X-ray image in each frame.

The dose of X-rays is not stabilized for the first frame 1. Conversely, where the last frame is frame M, imperfect irradiation (exposure) can take place for frame M when, for example, the irradiation button is released during irradiation. It is therefore desirable not to make a correction using the first frame 1 or last frame M as reference. Thus, in this embodiment, when the above M is a natural number satisfying K<M, the correcting unit 9a, (1) excluding the X-ray images in the first frame 1 and the last frame M, based on one X-ray image in frame K which is the frame preceding in time of the X-ray images in two, frame K and frame (K+1) adjoining each other in time, corrects the other X-ray image in frame (K+1) which is the frame succeeding in time (step S1 in FIG. 8). Then, (2) based on the above corrected one of the X-ray images which is the frame preceding in time of the X-ray images in two frames adjoining each other in time and including the corrected X-ray image in the frame preceding in time, the other X-ray frame which is the frame succeeding in time is corrected. This procedure is repeated until the X-ray image in the last frame M is corrected (steps S2 and S3 in FIG. 8).

Apart from the above, (3) excluding the X-ray images in the first frame 1 and the last frame M, based on one X-ray image OK in frame K which is the frame succeeding in time of the X-ray images in two, frame (K−1) and frame K adjoining each other in time, the other X-ray image in frame (K−1) which is the frame preceding in time is corrected (step T1 in FIG. 8). Then, (4) based on the above corrected one of the X-ray images which is the frame succeeding in time of the X-ray images in two frames adjoining each other in time and including the corrected X-ray image in the frame succeeding in time, the other X-ray frame which is the frame preceding in time is corrected. This procedure is repeated until the X-ray image in the first frame 1 is corrected (steps T2 and T3 in FIG. 8). Thus, through the corrections as in (1)-(4) (steps S1-S3 and T1-T3 in FIG. 8), the correcting unit 9a corrects the X-ray image in each frame using the X-ray image in frame K as reference. Since this frame K is neither the first frame 1 nor the last frame M, its X-ray image is appropriate as the reference, and therefore the corrections can he carried out appropriately.

It is preferable to carry out (1) and (3) above (i.e. steps S1 and T1 in FIG. 8) in parallel as in this embodiment. The calculation time in the correcting unit 9a can be shortened by carrying out (1) and (3) (i.e. steps S1 and T1 in FIG. 8) in parallel. Of course, (3) and (4) (steps T1-T3 in FIG. 8) may be carried out after (1) and (2) (steps S1-S3 in FIG. 8). Conversely, (1) and (2) (steps S1-S3 in FIG. 8) may be carried out after (3) and (4) (steps T1-T3 in FIG. 8).

In the case where (1) and (3) (i.e. steps S1 and T1 in FIG. 8) are carried out in parallel, and when M is an odd number, it is preferable to determine an X-ray image acting as reference for the correction in a way to satisfy K=(M+1)/2. That is, since the X-ray image in frame K which satisfies K=(M+1)/2 is at the center in time, by carrying out (1) and (3) (i.e. steps S1 and T1 in FIG. 8) in parallel, the correction of the X-ray image in the last frame M in (2) and the correction of the X-ray image in the first frame 1 in (4) can be finished at the same time, and the calculation time in the correcting unit 9a can be shortened further.

In the case where (1) and (3) (i.e. steps S1 and T1 in FIG. 8) are carried out in parallel, and when M is an even number, it is preferable to determine an X-ray image acting as reference for the correction in a way to satisfy K=M/2+1 or K=M/2. That is, since the X-ray image in frame K which satisfies K=M/2+1 or K=M/2 is substantially at the center in time, by carrying out (1) and (3) (i.e. steps S1 and T1 in FIG. 8) in parallel, the correction of the X-ray image in the last frame M in (2) and the correction of the X-ray image in the first frame 1 in (4) can be finished substantially at the same time, and the calculation time in the correcting unit 9a can be shortened further.

In this embodiment, the X-ray tube 2 and FPD 3 are movable parallel to each other at the same speed. With the X-ray tube 2 and FPD 3 moving parallel to each other at the same speed, the projection angle can be maintained at the same angle. The X-ray tube 2 and FPD 3 can be moved for a long time. As a result, a sectional image with a longer field of view can be obtained.

This invention is not limited to the foregoing embodiment, but may be modified as follows:

(1) In the foregoing embodiment, the X-ray tomography apparatus has been described as an example of radiographic apparatus. The invention may be applied to a radiographic apparatus, such as an ECT (Emission Computed Tomography) apparatus represented by a PET (Positron Emission Tomography) apparatus or a SPECT (Single Photon Emission CT) apparatus, which carries out radiation image pickup by detecting radiation other than X-rays (gamma rays in the case of the PET apparatus) and obtaining radiographic images based on the detected radiation.

(2) In the foregoing embodiment, the flat panel X-ray detector has been described as an example of radiation detecting device. There is no limitation as long as the device is an X-ray detecting device used generally, such as an image intensifier (I.I). As in the case of being applied to an ECT apparatus, as in modification (1) above, there is no limitation as long as it is a radiation detecting device used generally.

(3) The foregoing embodiment provides the output device represented by the monitor 13. The output device is not absolutely necessary.

(4) In the foregoing embodiment, the radiation emitting device represented by the X-ray tube 2 and the radiation detecting device represented by the FPD 3 are moved parallel to each other at the same speed. As long as the radiation emitting device and radiation detecting device are moved parallel relative to each other in the same direction along the longitudinal direction of the patient, one of them may be moved fast and the other moved slowly.

(5) In the foregoing embodiment, only the radiation emitting device represented by the X-ray tube 2 and the radiation detecting device represented by the FPD 3 are moved, and the top board 1 supporting the patient M is fixed, whereby the radiation emitting device and radiation detecting device are moved parallel relative to each other in the same direction along the longitudinal direction of the patient. The invention is not limited to a specific movement as long as the radiation emitting device and radiation detecting device are moved parallel relative to each other in the same direction along the longitudinal direction of the patient. For example, the radiation emitting device represented by the X-ray tube 2 and the radiation detecting device represented by the FPD 3 may be fixed, and only the top board 1 supporting the patient M may be moved, whereby the radiation emitting device and radiation detecting device are moved parallel relative to each other in the same direction along the longitudinal direction of the patient. The radiation emitting device represented by the X-ray tube 2 and the radiation detecting device represented by the FPD 3 may be moved, and the top board 1 supporting the patient M may also be moved in the longitudinal direction, whereby the radiation emitting device and radiation detecting device are moved parallel relative to each other in the same direction along the longitudinal direction of the patient.

(6) In the foregoing embodiment, the correction is carried out using all the overlapping areas. However, it is not necessary to carry out the correction using all. From the overlapping areas predetermined pixel areas smaller than those areas (e.g. areas around the center in a transverse direction perpendicular in a horizontal plane to the longitudinal direction) may be selected, and the correcting unit 9a may correct the X-ray images based only on the selected pixel areas. By carrying out the correction without using all the overlapping areas, the arithmetic process by the correcting unit 9a can be made high-speed.

(7) In the foregoing embodiment, a radiographic image (X-ray image in the embodiment) acting as reference for the correction, i.e. the frame at the center, is determined in a way to satisfy K=(M+1)/2 when M is an odd number, and to satisfy K=M/2+1 or K=M/2 when M is an even number. However, the radiographic image (X-ray image) acting as reference for the correction is not limited to the image in the central frame. If it is not necessarily required to end the correction of the X-ray image in the last frame M in (2), and the correction of the X-ray image in the first frame 1 in (4) substantially at the same time, the radiographic image (X-ray image) in any frame may be used as reference for the correction.

(8) In the foregoing embodiment, a radiographic image (X-ray image) acting as reference for the correction is determined, excluding the radiographic images (X-ray images in the embodiment) in the first frame 1 and the last frame M, and the radiographic image (X-ray image) in each frame is corrected with reference to the radiographic image (X-ray image). if there is no problem in using the first frame 1 or last frame M as reference for the correction, the radiographic image (X-ray image) in the first frame 1 may be used as reference and the succeeding frames may be corrected sequentially. Conversely, the radiographic image (X-ray image) in the last frame M may be used as reference and the preceding frames may be corrected sequentially.

(9) In the foregoing embodiment, based on one radiographic image (X-ray image in the embodiment) of the radiographic images (X-ray images) in two, frame K and frame (K+1) adjoining each other in time, the other radiographic image (X-ray image) is corrected, and the radiographic images (X-ray images) in all the frames are corrected by repeating the procedure in which, based on one radiographic image (X-ray image) of the radiographic images (X-ray images) in two frames adjoining each other in time, including the corrected radiographic image (X-ray image), the other radiographic image (X-ray image) is corrected. However, it is not necessary to correct the radiographic images (X-ray images) in all the frames. Only with frames having luminance differences, based on one radiographic image (X-ray image) of the radiographic images (X-ray images) in two, frame K and frame (K+1) adjoining each other in time, the other radiographic image (X-ray image) may be corrected.

(10) In the foregoing embodiment, based on one radiographic image (X-ray image) of the radiographic images (X-ray images in the embodiment) in two, frame K and frame (K+1) adjoining each other in time, the other radiographic image (X-ray image) is corrected. However, the correction between the two frames adjoining each other in time is not limitative. Radiographic images (X-ray images) continually and successively acquired may be selected at every predetermined frame interval, and the radiographic images (X-ray images) may be corrected based on overlapping areas between a plurality of selected radiographic images (X-ray images).

The invention claimed is:

1. A radiographic apparatus having a radiation emitting device for emitting radiation toward a patient, and a radiation detecting device for detecting radiation transmitted through the patient, to carry out radiation image pickup by obtaining radiographic images based on the detected radiation, the radiation emitting device and the radiation detecting device being constructed movable parallel relative to each other in the same direction along a longitudinal direction of the patient, the radiation emitting device emitting radiation and the radiation detecting device detecting radiation transmitted through the patient irradiated while the radiation emitting device and the radiation detecting device move every predetermined distance relative to the patient, said apparatus comprising a correcting device for correcting radiographic images based on overlapping areas of a plurality of radiographic images based on the radiation detected whenever a relative movement is made in the same direction along a longitudinal direction of the patient, an image decomposing device for decomposing corrected radiographic images for the every predetermined distance, an image composing device for composing the decomposed images for each of the same projection angles to obtain a projection image for each projection angle, and a reconstruction processing device for carrying out a reconstruction process based on the composed projection images to obtain a sectional image.

2. The radiographic apparatus according to claim 1, wherein, when K is a natural number, the correcting device is arranged, based on one radiographic image of radiographic images in two, frame K and frame (K+1) adjoining each other in time, to correct the other radiographic image.

3. The radiographic apparatus according to claim 2, wherein the correcting device is arranged, based on the one radiographic image of the radiographic images in the two, frame K and frame (K+1) adjoining each other in time, to correct the other radiographic image, and to repeat a procedure in which, based on one radiographic image of radiographic images in two frame adjoining each other in time, including the corrected radiographic image, the other radiographic image is corrected.

4. The radiographic apparatus according to claim 3, wherein, when K is a natural number satisfying K<M, the correcting device is arranged, (1) excluding radiographic images in a first frame 1 and a last frame M, based on one radiographic image in a frame K which is the frame preceding in time of the radiographic images in the two, frame K and frame (K+1) adjoining each other in time, to correct the other radiographic image in frame (K+1) which is the frame succeeding in time, (2) to repeat a procedure, until the radiographic image in the last frame M is corrected, in which, based on the corrected one of the radiographic images which is the frame preceding in time of the radiographic images in two frames adjoining each other in time and including the corrected radiographic image in the frame preceding in time, the other radiographic frame which is the frame succeeding in time is corrected, (3) excluding the radiographic images in the first frame 1 and the last frame M, based on one radiographic image in the frame K which is the frame succeeding in time of the radiographic images in two, frame (K−1) and frame K adjoining each other in time, to correct the other radiographic image in frame (K−1) which is the frame preceding in time, and (4) to repeat a procedure, until the radiographic image in the first frame 1 is corrected, in which, based on the corrected one of the radiographic images which is the frame succeeding in time of the radiographic images in two frames adjoining each other in time and including the corrected radiographic image in the frame succeeding in time, the other radiographic frame which is the frame preceding in time is corrected, whereby the correcting device corrects the radiographic image in each frame using the radiographic image in the frame K as reference.

5. The radiographic apparatus according to claim 4, wherein the correcting device is arranged to carry out (1) and (3) above in parallel.

6. The radiographic apparatus according to claim 5, wherein, when M is an odd number, a radiographic image acting as reference for the correction is determined in a way to satisfy $K=(M+1)/2$.

7. The radiographic apparatus according to claim 5, wherein, when M is an even number, a radiographic image acting as reference for the correction is determined in a way to satisfy one of $K=M/2+1$ and $K=M/2$.

8. The radiographic apparatus according to claim 1, wherein from the overlapping areas of the, plurality of radiographic images predetermined pixel areas smaller than the areas are selected, and the correcting device is arranged to correct the radiographic images based only on the selected pixel areas.

9. The radiographic apparatus according to claim 1, wherein the radiation emitting device and the radiation detecting device are movable parallel to each other at the same speed relative to the patient.

* * * * *